(12) United States Patent
Gotfried

(10) Patent No.: US 9,931,209 B2
(45) Date of Patent: Apr. 3, 2018

(54) ORTHOPEDIC IMPLANTS

(71) Applicant: Yechiel Gotfried, Kiryat Motzkin (IL)

(72) Inventor: Yechiel Gotfried, Kiryat Motzkin (IL)

( * ) Notice: Subject to any disclaimer, the term of this patent is extended or adjusted under 35 U.S.C. 154(b) by 0 days.

(21) Appl. No.: 15/435,599

(22) Filed: Feb. 17, 2017

(65) Prior Publication Data

US 2017/0189188 A1 Jul. 6, 2017

Related U.S. Application Data

(62) Division of application No. 14/836,664, filed on Aug. 26, 2015, now abandoned.

(60) Provisional application No. 62/097,322, filed on Dec. 29, 2014.

(51) Int. Cl.

| A61F 2/38 | (2006.01) |
|---|---|
| A61F 2/28 | (2006.01) |
| A61F 2/44 | (2006.01) |
| A61F 2/42 | (2006.01) |
| A61F 2/30 | (2006.01) |
| A61B 17/80 | (2006.01) |

(52) U.S. Cl.
CPC .............. *A61F 2/28* (2013.01); *A61F 2/4225* (2013.01); *A61F 2/4455* (2013.01); *A61B 17/8095* (2013.01); *A61F 2002/2892* (2013.01); *A61F 2002/30158* (2013.01); *A61F 2002/30266* (2013.01); *A61F 2002/30736* (2013.01); *A61F 2002/4233* (2013.01)

(58) Field of Classification Search
CPC .................. A61F 2002/30736; A61B 17/8095
See application file for complete search history.

(56) References Cited

U.S. PATENT DOCUMENTS

| 6,039,762 A | 3/2000 | McKay |
|---|---|---|
| 6,902,578 B1 | 6/2005 | Anderson et al. |
| 2004/0006390 A1 | 1/2004 | Duarte |
| 2004/0193270 A1 | 9/2004 | Dimauro et al. |

(Continued)

FOREIGN PATENT DOCUMENTS

| FR | 2919488 A1 | 2/2009 | |
|---|---|---|---|
| WO | WO 2007/064950 A2 * | 6/2007 | ......... A61B 17/8095 |
| WO | 2013179142 A1 | 12/2013 | |

OTHER PUBLICATIONS

U.S. Appl. No. 61/653,077, filed May 30, 2012.*

(Continued)

*Primary Examiner* — David H Willse
(74) *Attorney, Agent, or Firm* — Holtz, Holtz & Volek PC

(57) ABSTRACT

Method for rotating and increasing a distance of a patella from the trochlea of a subject includes creating an osteotomy in a tibia of the subject, and inserting, along an axis of insertion, an orthopedic implant into the osteotomy, bone graft material being coupled to the orthopedic implant. The method also includes rotating a patella of the subject, via a patellar tendon of the subject, about the axis of insertion, by rotating a tuberosity of the tibia of the subject about the axis of insertion, and increasing a distance of the patella from a trochlea of a femur of the subject, via the patellar tendon of the subject, by pivoting the tuberosity of the tibia with respect to a point of contact between the tuberosity of the tibia and another portion of the tibia. The implant is shaped to define one or more passageways passing through the implant.

8 Claims, 11 Drawing Sheets

(56) References Cited

U.S. PATENT DOCUMENTS

| | | | |
|---|---|---|---|
| 2005/0010223 A1 | 1/2005 | Gotfried | |
| 2005/0010292 A1 | 1/2005 | Carrasco | |
| 2005/0246021 A1 | 11/2005 | Ringeisen et al. | |
| 2005/0261767 A1 | 11/2005 | Anderson et al. | |
| 2007/0016295 A1 | 1/2007 | Boyd | |
| 2007/0050029 A1 | 3/2007 | Carrasco | |
| 2008/0195099 A1 | 8/2008 | Minas | |
| 2009/0177203 A1* | 7/2009 | Reiley | A61B 17/8095 606/87 |
| 2010/0152853 A1 | 6/2010 | Kirschman | |
| 2010/0305712 A1 | 12/2010 | Ringeisen et al. | |
| 2011/0004311 A1 | 1/2011 | Semler et al. | |
| 2012/0184962 A1* | 7/2012 | Merchant | A61B 17/152 606/88 |
| 2013/0116793 A1 | 5/2013 | Kloss | |
| 2013/0184826 A1 | 7/2013 | Thaiyananthan | |
| 2016/0089166 A1* | 3/2016 | Maxson | A61B 17/1764 606/88 |
| 2016/0128748 A1* | 5/2016 | Tepic | A61B 17/8095 206/570 |

OTHER PUBLICATIONS

U.S. Appl. No. 14/836,664, First Named Inventor: Yechiel Gotfried, Title: "Orthopedic Implants", filed Aug. 26, 2015.
U.S. Appl. No. 15/189,641, First Named Inventor: Yechiel Gotfried, Title: "Orthopedic Implants", filed Jun. 22, 2016.

* cited by examiner

ORTHOPEDIC IMPLANTS

CROSS-REFERENCE TO RELATED APPLICATIONS

This is a Divisional application of U.S. Ser. No. 14/836,664, filed Aug. 26, 2015, which claims the benefit of provisional application Ser. No. 62/097,322, filed Dec. 29, 2014, the entire contents of both of which are incorporated herein by reference.

FIELD OF THE INVENTION

Applications of the present invention relate in general to orthopedic implants, and specifically, to orthopedic implants for changing an angular orientation of a bone.

BACKGROUND

In some pathologies, the patella is too close to the trochlea of the femur, and/or is improperly aligned with respect to the trochlea. In other pathologies, an intervertebral space in the spinal column too small, and/or normal lordosis of the spinal column absent. Multiple other pathologies relate to inappropriately aligned bones.

SUMMARY OF THE INVENTION

Applications of the present invention include methods for operating on a subject, in order to treat pathological conditions. For example, an orthopedic implant may be inserted into an osteotomy in a tibia of the subject, bone graft material being coupled to the implant. By implanting the implant in the osteotomy, the patella of the subject is rotated about the axis of insertion, and a distance of the patella from the anterior distal portion of the femur (i.e., the trochlea of the femur) is increased. The orthopedic implant includes a front end, a rear end, a top, a bottom, a right side, and a left side. To facilitate the rotation of the patella, the distance between the top and the bottom is greater at one of the sides than at the other one of the sides. The implant is shaped to define one or more passageways passing through the implant, the passageways facilitating the coupling of bone graft material to the implant.

There is therefore provided, in accordance with some applications of the present invention, apparatus for implanting in an anatomical site, the apparatus including:
an orthopedic implant, including
a front end,
a rear end,
a top,
a bottom,
a right side, and
a left side,
a distance between the top and the bottom being (a) greater at a first location at one of the sides than at a second location opposite the first location at the other one of the sides, and (b) greater at a third location at the front end than at a fourth location opposite the third location at the rear end,
the implant being shaped to define one or more passageways passing through the implant.

In some applications, at least one of the passageways passes from the top to the bottom.

In some applications, the distance between the top and the bottom is at least 0.5% greater at the first location than at the second location.

In some applications, the distance between the top and the bottom is at least 0.5% greater at the third location than at the fourth location.

In some applications, the distance between the top and the bottom is greater at the first location than at the second location along at least 80% of one of the sides.

In some applications, the distance between the top and the bottom is greater at the third location than at the fourth location along at least 80% of the front end.

In some applications, a distance between the sides is greater at the front end than at the rear end.

In some applications, at least one of the passageways has (a) an opening at the top, an edge of the opening that is on the top completely surrounding the opening at the top, and (b) an opening at the bottom, an edge of the opening that is on the bottom completely surrounding the opening at the bottom.

In some applications, at least one of the passageways has (a) an opening at the top, an edge of the opening that is on the top not completely surrounding the opening at the top, and (b) an opening at the bottom, an edge of the opening that is on the bottom not completely surrounding the opening at the bottom.

In some applications, at least 80% of a portion of the implant selected from the group consisting of: the front end, the rear end, the top, the bottom, the right side, and the left side is shaped to define openings to at least some of the passageways.

In some applications, at least 90% of the selected portion is shaped to define openings to at least some of the passageways.

In some applications, the implant is shaped to define at least 5 passageways.

In some applications, the implant is shaped to define at least 10 passageways.

In some applications, the apparatus further includes a connection interface that facilitates a connection of the implant to a tool.

In some applications, the connection interface shaped to define a threaded hole.

In some applications, the connection interface is front-facing.

In some applications, the distance between the top and the bottom is at least 0.5 mm greater at the first location than at the second location.

In some applications, the distance between the top and the bottom is at least 2.5 mm greater at the first location than at the second location.

In some applications, the apparatus further includes a bone graft material.

In some applications, the bone graft material is disposed within the passageways.

In some applications, the implant consists of a metal.
In some applications, the implant consists of a plastic.
In some applications, the implant consists of bone graft material.

There is further provided, in accordance with some applications of the present invention, apparatus for implanting in an anatomical site, the apparatus including:
an orthopedic implant, including:
a front end,
a rear end,
a top,
a bottom,
a right side, and
a left side, a distance between the top and the bottom being greater at a first location at one of the sides than at a second location opposite the first location at the other one of the sides, along at least 80% of one of the sides, the implant being shaped to define one or more passageways passing through the implant; and a front-facing connection interface that facilitates a connection of the implant to a tool.

There is further provided, in accordance with some applications of the present invention, a method for operating on a subject, the method including:

providing an orthopedic implant; and by inserting, along an axis of insertion, the orthopedic implant into an anatomical site, changing an angular orientation of a first portion of bone with respect to a second portion of bone by rotating the first portion of bone about (a) the axis of insertion, and (o) an axis that as perpendicular to the axis of insertion.

In some applications, the method further includes, by inserting the implant into the site, increasing a distance of the first portion of bone from the second portion of bone.

In some applications, inserting the orthopedic implant into the anatomical site includes inserting the orthopedic implant into an anatomical site that is surrounded at least in part by one or more bones.

In some applications, the method further includes creating an osteotomy at the anatomical site prior to inserting the orthopedic implant into the anatomical site.

In some applications, the anatomical site is a space between a first vertebra and a second vertebra of the subject, the first portion of bone is the first vertebra, the second portion of bone is the second vertebra, and the method includes increasing a distance between the first and second vertebra, and changing an angular orientation of the first vertebra with respect to the second vertebra, by inserting the implant.

In some applications, the method further includes, before inserting the implant, enlarging the space.

In some applications, the method further includes inserting a bone graft material into the anatomical site.

In some applications, inserting the bone graft material includes inserting bone graft material that is coupled to the implant.

In some applications, the anatomical site is an osteotomy within a metatarsal bone of the subject, the first portion of bone is a first portion of the metatarsal bone, the second portion of bone is a second portion of the metatarsal bone, and the method includes changing an angular orientation of the first portion of the metatarsal bone with respect to the second portion of the metatarsal bone by inserting the implant.

In some applications, the anatomical site is an osteotomy within a tibia of the subject, the first portion of bone is a first portion of the tibia, the second portion of bone is a second portion of the tibia that is more distal than the first portion of the tibia, and the method includes changing an angular orientation of the first portion of the tibia with respect to the second portion of the tibia by inserting the implant.

There is further provided, in accordance with some applications of the present invention, a method for operating on a subject, the method including:

creating an osteotomy in a tibia of the subject; and by inserting, along an axis of insertion, an orthopedic implant into the osteotomy:

changing an angular orientation of a patella of the subject with respect to a trochlea of a femur of the subject by rotating the patella about the axis of insertion, by:

changing an angular orientation of a tuberosity of the tibia of the subject with respect to another portion of the tibia by rotating the tuberosity of the tibia about the axis of insertion, and increasing a distance of the patella from the trochlea by pivoting the tuberosity of the tibia with respect to a point of contact between the tuberosity of the tibia and another portion of the tibia.

In some applications, the method further includes inserting a bone graft material into the anatomical site.

In some applications, inserting the bone graft material includes inserting bone graft material that is coupled to the implant.

There is further provided, in accordance with some applications of the present invention, a method for operating on a subject, the method including:

creating an osteotomy in a tibia of the subject; and by inserting, along an axis of insertion, an orthopedic implant into the osteotomy, bone graft material being coupled to the implant:

rotating a patella of the subject, via a patellar tendon of the subject, about the axis of insertion, by rotating a tuberosity of the tibia of the subject about the axis of insertion, and increasing a distance of the patella from a trochlea of a femur of the subject, via the patellar tendon of the subject, by pivoting the tuberosity of the tibia with respect to a point of contact between the tuberosity of the tibia and another portion of the tibia.

The present invention will be more fully understood from the following detailed description of applications thereof, taken together with the drawings, in which:

DETAILED DESCRIPTION OF THE DRAWINGS

Figure 1A:
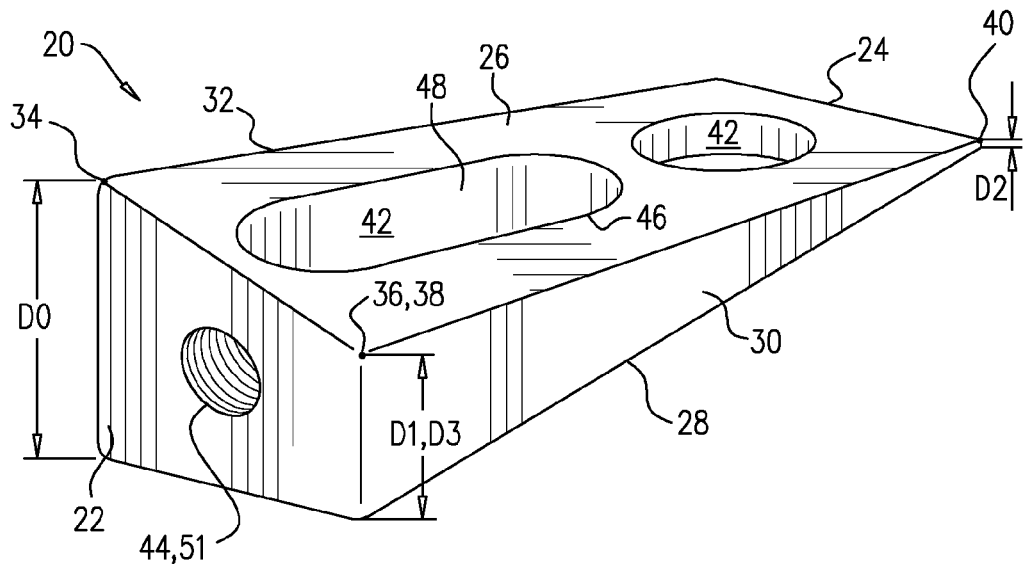
FIGS. 1A-F, 2A-B, 3A-B, and 4A-B are schematic illustrations of an orthopedic implant for implanting in an anatomical site, in accordance with some applications of the present invention.

Reference is made to FIGS. 1A-4B, which are schematic illustrations of an orthopedic implant 20 for implanting in an anatomical site, in accordance with some applications of the present invention. Typically, the anatomical site is surrounded at least in part by one or more bones. For example, implant 20 may be implanted in a bone (e.g., an osteotomy, such as an osteotomy in a tibia), or a space between bones.

Implant 20 comprises a front end 22, a rear end 24, a top 26, a bottom 28, a right side 30, and a left side 32. As further described hereinbelow, e.g., with reference to FIG. 7, one function of implant 20 is to change an angular orientation of one bone portion (i.e., part or all of a bone) with respect to another bone portion. To facilitate this function, a distance D0 between top 26 and bottom 28 at one of the sides is greater than a distance D1 between the top and bottom at the other side, along at least a portion of the sides. (For convenience, the distance between the top and bottom of the implant may be referred to below as the "height" of the implant.) In particular, D0 at a first location 34 at one of the sides is greater than D1 at a second location 36 opposite the first location at the other one of the sides. In some applications, D0 is greater than D1 along at least 80% of one of the sides. In some applications, for at least one instance of the first location and second location, D0 is at least 0.5 mm greater, e.g., at least 2.5 mm greater, and/or less than 20 mm greater, than D1. In other words, at at least one pair of opposite locations, the height at one of the sides is at least 0.5 mm greater and/or less than 20 mm greater than the height of the other one of the sides. Alternatively or additionally, at at least one pair of opposite locations, D0 is at least 0.5% greater than D1.

Typically, implant 20 is also shaped such that a distance D3 between the top and bottom at the front end is greater (e.g., 0.5% greater) than a distance D2 between the top and bottom at the rear end, along at least a portion of the ends in particular, D3 at a third location 38 at the front end is greater than D2 at a fourth location 40 opposite the third location at the rear end. In some applications, D3 is greater than D2 along at least 80% of one of the ends. In general, this shape facilitates changing a second angular orientation of a bone portion, and/or facilitates the wedging of the implant within an anatomical site. In some applications, a distance D7 between the sides at the front end is greater than the distance D4 between the sides at the rear end.

Typically, bone graft material is inserted into the anatomical site along with the implant, the bone graft material helping to stimulate bone formation in the anatomical site. (It is noted that in the context of the claims and specification of the present application, "bone graft material" includes any type of bone graft or bone graft substitute.) Typically, the implant is shaped to define one or more passageways 42 passing through the implant, and the bone graft material is disposed within passageways 42. Typically, at least one of the passageways passes from the top to the bottom.

Figure 2A:
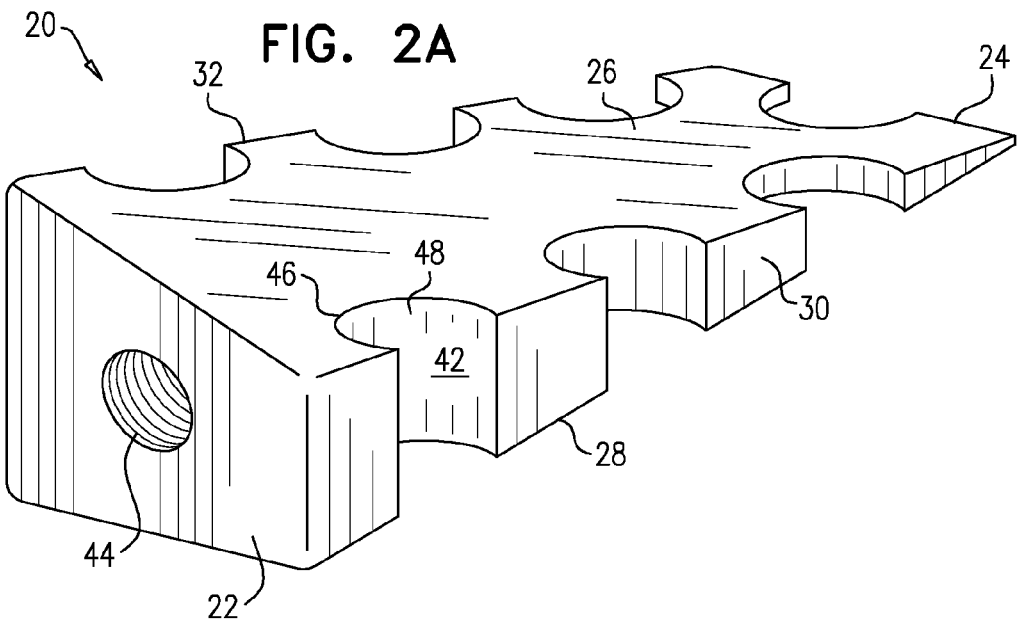

In some applications, at least one of passageways 42 has "enclosed" openings; for example, FIG. 1A shows implant 20 having two such passageways. A passageway having enclosed openings is a passageway that has (a) an opening 48 at top 26, an edge 46 of opening 48 completely surrounding opening 48, and (b) an opening at bottom 28 (not shown), an edge of the opening that is on the bottom completely surrounding the opening at the bottom. Alternatively or additionally, e.g., as shown in FIG. 2A, at least one of the passageways has "unenclosed" openings. A passageway having unenclosed openings is a passageway that has (a) an opening 48 at the top, an edge 46 of the opening not completely surrounding the opening, and (b) an opening at the bottom (not shown), an edge of the opening that is on the bottom not completely surrounding the opening at the bottom. In some applications, at least one passageway has one enclosed opening and another unenclosed opening.

Figure 4A:
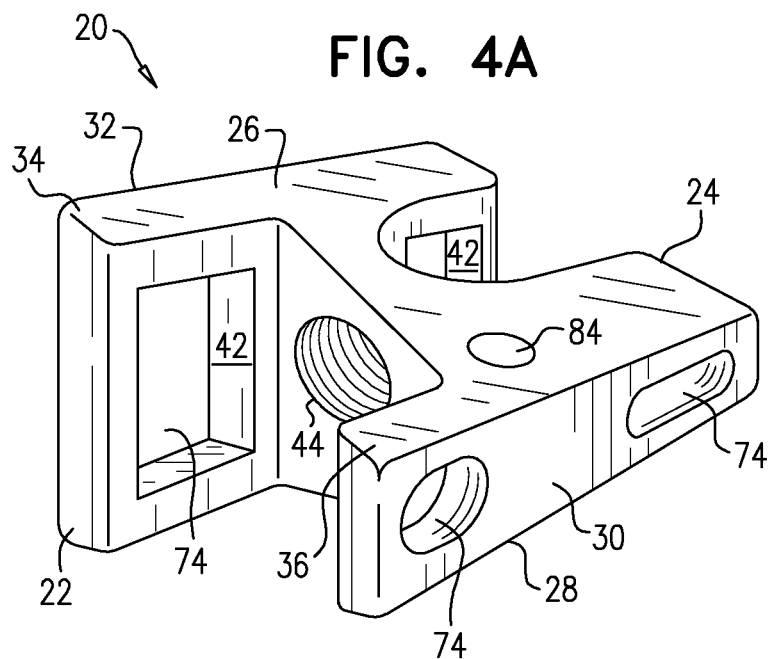

In some applications, at least 80% (e.g., at least 90%) of the front end, rear end, top, bottom, right side, and/or left side is shaped to define openings to at least some of the passageways. For example, FIGS. 1E-F show the implant having porous top and bottom surfaces that are shaped similarly to the surface of a honeycomb. Such applications typically allow for a relatively large amount of bone graft material to be inserted into the anatomical site. Alternatively or additionally, to facilitate insertion of bone graft material, the implant may be shaped to define a relatively large number of passageways, e.g., at least 5, 10, or more. Alternatively or additionally, the openings to the passageways may be relatively large, to facilitate insertion of bone graft material, and/or to facilitate access and/or coupling of a tool (e.g., an implantation tool) to the implant. For example, FIG. 4A shows large lateral openings 74.

Figure 4B:
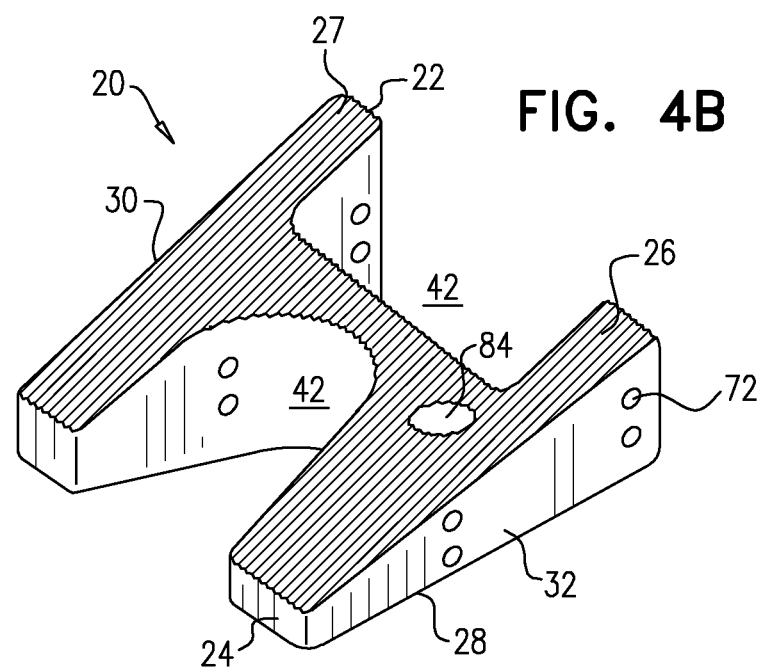

In some applications, more than two surfaces are shaped to define openings to passageways. For example, FIGS. 1F and 4B show lateral openings 72, in addition to the "main" openings on the top and bottom surfaces. Openings 72 may be used for passing a wire or thread therethrough, to facilitate holding the bone graft in place within passageways 42. (As noted above, FIG. 4A also shows lateral openings 74, in addition to the "main" openings.)

In some applications, some of the openings may be used for passing a drill-alignment tool therethrough. For example, FIGS. 3A-B and 4A-B show openings 84, which may be used for this purpose. For example, alignment techniques described in US 2005/0010223 to Gotfried, which is incorporated herein by reference, and shown in FIGS. 6 and 8 thereof, may be used for this purpose.

Typically, implant 20 comprises a connection interface 44, such as a threaded hole 51, that facilitates a connection of the implant to a tool, e.g., an implantation tool. Although connection interface 44 is typically front-facing, it may also face in a different direction; for example, side-facing lateral openings 74 (FIG. 4A) may be considered connection interfaces.

In some applications, the implant consists entirely of a metal, e.g., a metallic alloy and/or titanium. In other applications, the implant consists entirely of a plastic (e.g., polyether ether ketone), or entirely of bone graft material.

Figure 1B:
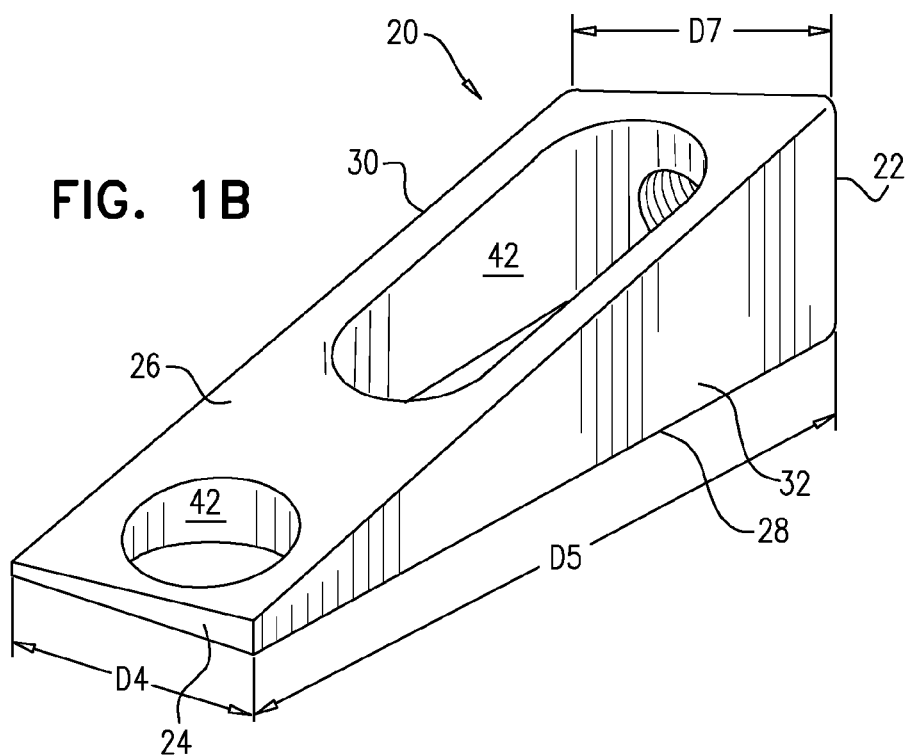
Figure 1C:
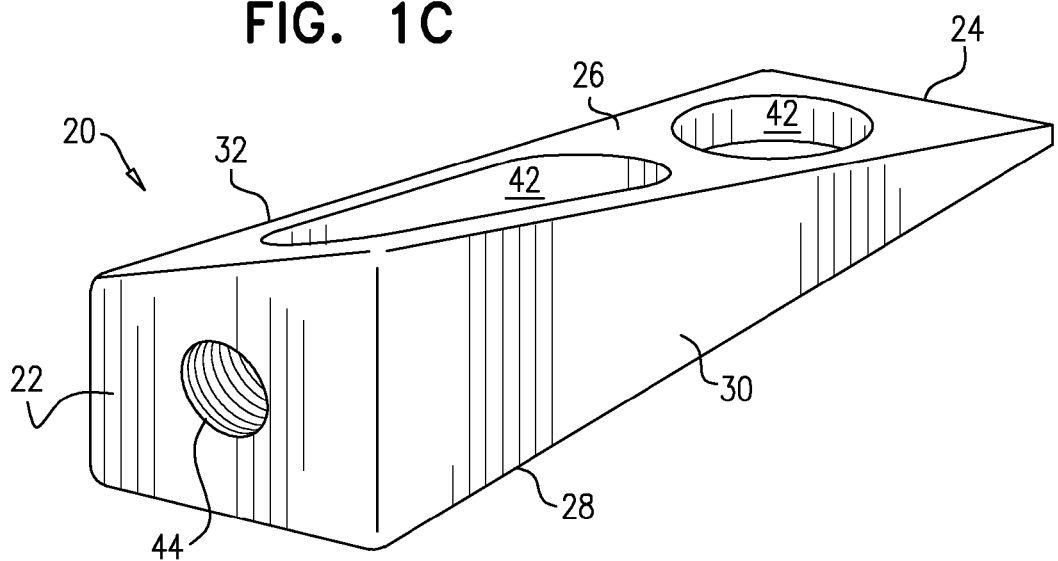
Figure 1D:
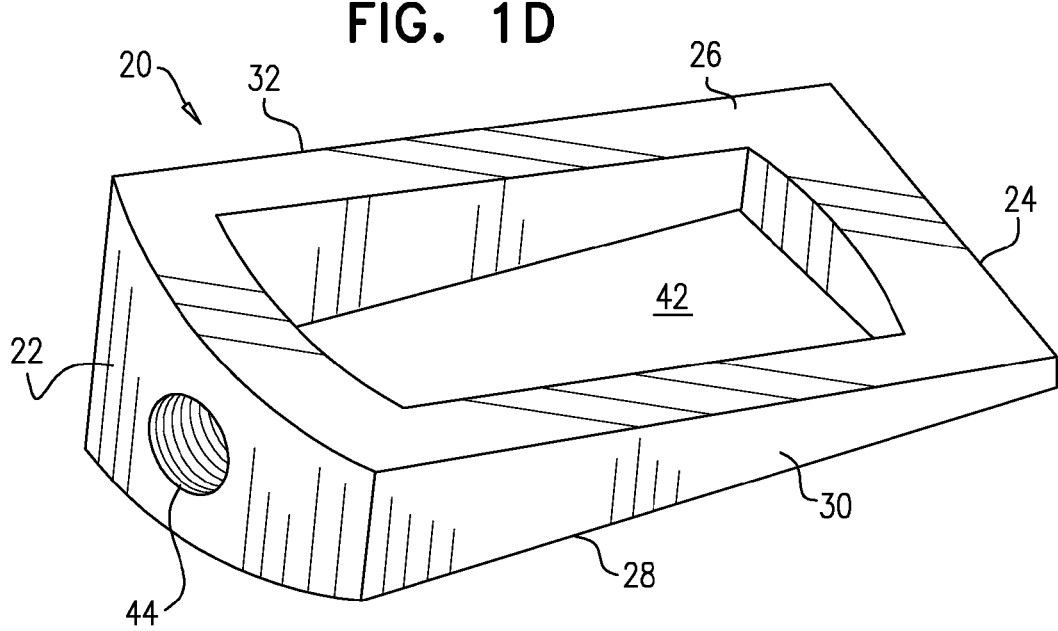
Figure 1E:
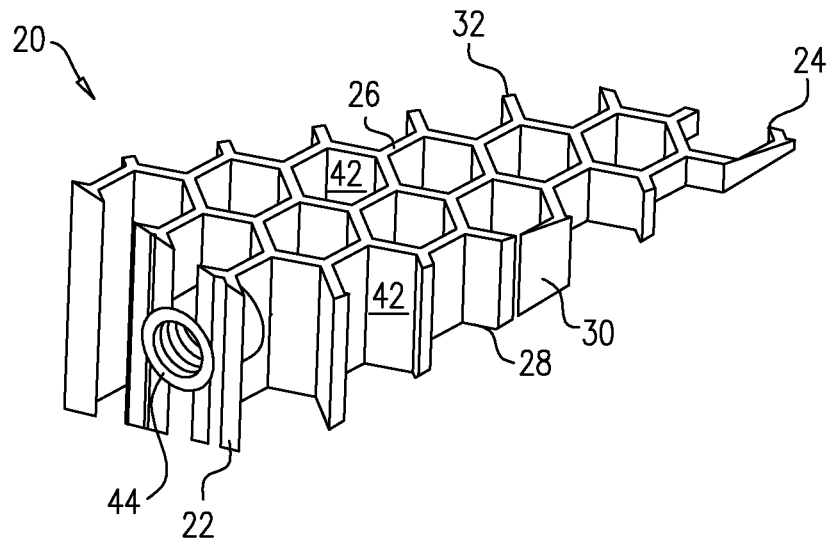
Figure 1F:
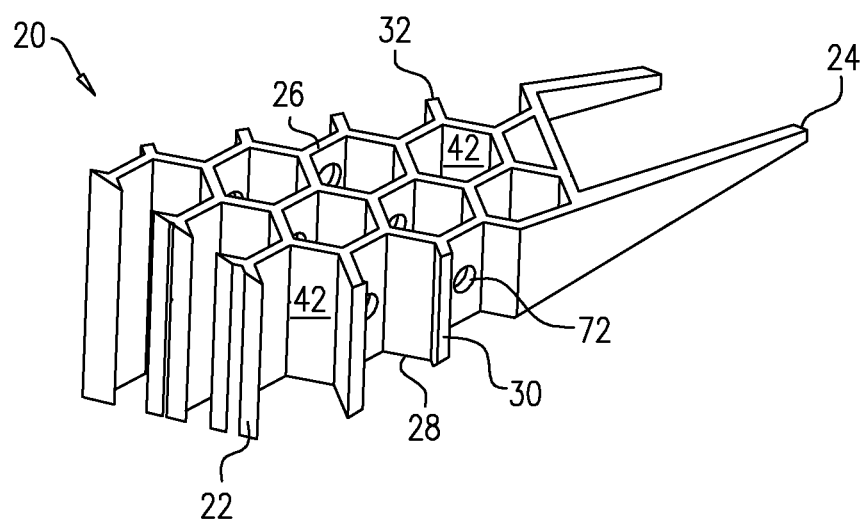
Figure 2B:
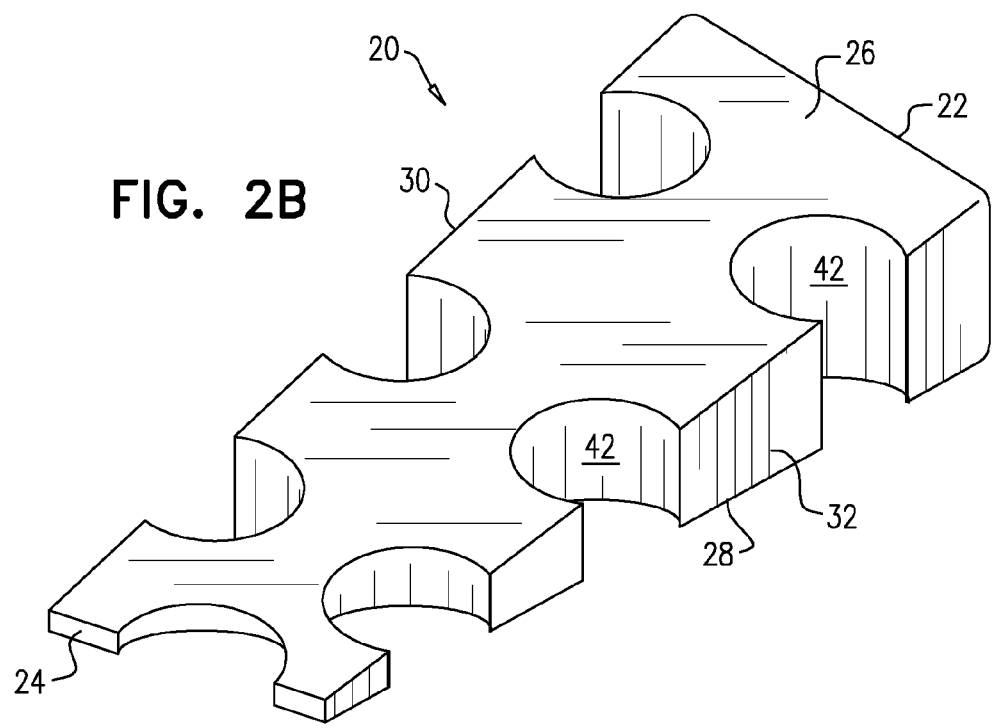
Figure 3A:
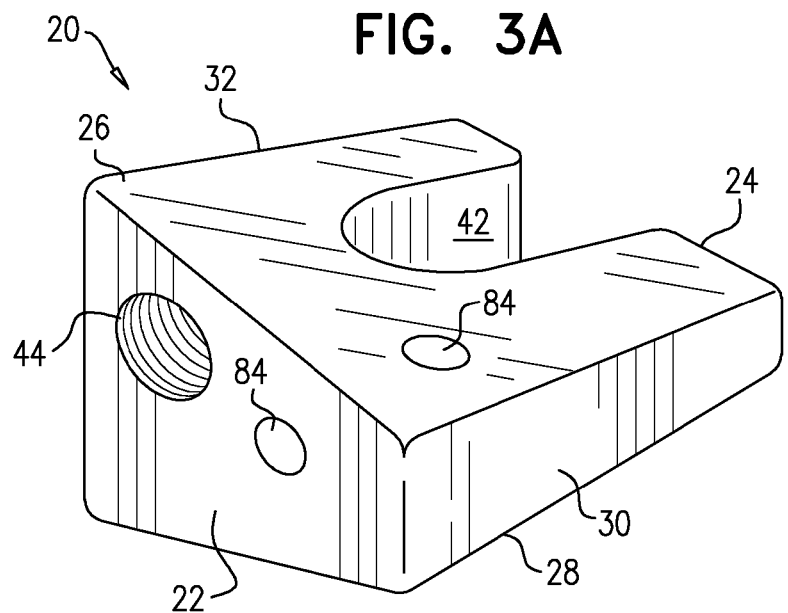
Figure 3B:
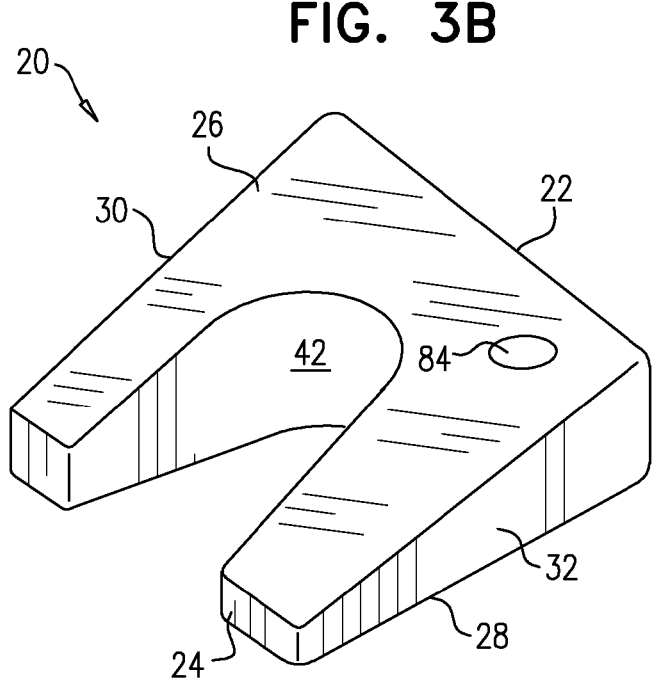

It is noted that FIG. 1B shows the same implant shown in FIG. 1A, from the opposite viewpoint. FIG. 1C, on the other hand, shows an approximate mirror-image of the implant shown in FIG. 1A. Thus, for example, if the implant of FIG. 1A is appropriate for the right tibia of a subject, the implant of FIG. 1C may be appropriate for the left tibia. Similarly, FIGS. 2A-B are approximate mirror images of one another, as are FIGS. 3A-B and FIGS. 4A-B.

In some applications, as shown in FIG. 4B, one or more surfaces of the implant (e.g., the top and/or bottom of the implant) is shaped to define ridges 27, which facilitate better contact of the implant with the surrounding bone.

Figure 5:
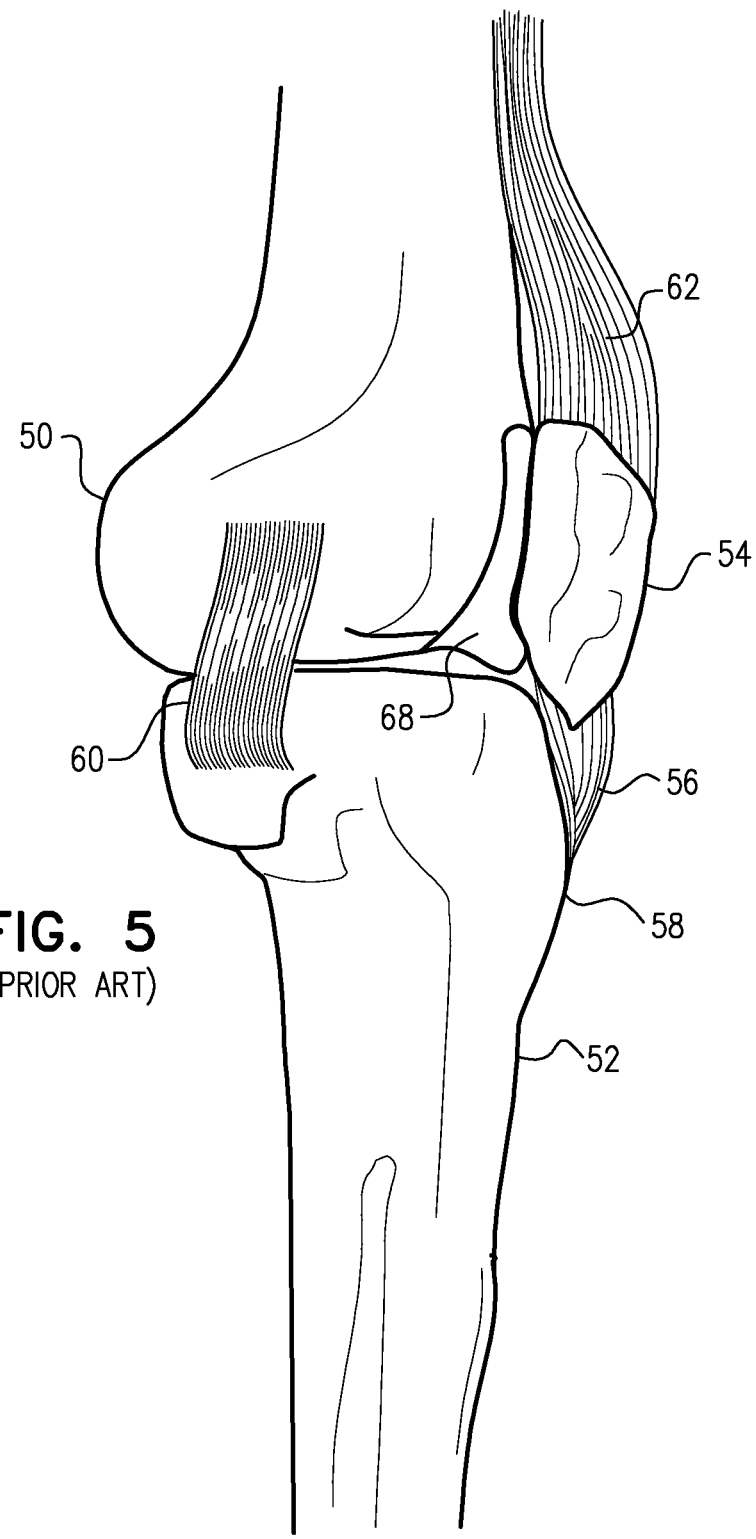
FIG. 5 is a schematic illustration of a portion of human anatomy.

Reference is now made to FIG. 5, which is a schematic illustration of a portion of human anatomy. FIG. 5 shows the tibia 52, which includes the tibial tuberosity 58, which is a large oblong elevation on the proximal, anterior aspect of tibia 52. The tibia is joined to the femur 50 via, inter alia, the lateral collateral ligament 60. The patellar tendon 56 joins tibial tuberosity 58 to the patella 54, which, in turn, is joined to femur 50 via the quadriceps tendon 62. In some pathologies, the patella is too close to the trochlea 68 of the femur (i.e., the anterior distal portion of the femur), and/or is improperly aligned with respect to trochlea 68. Applications of the present invention address this pathology, as will now be described.

Figure 6:
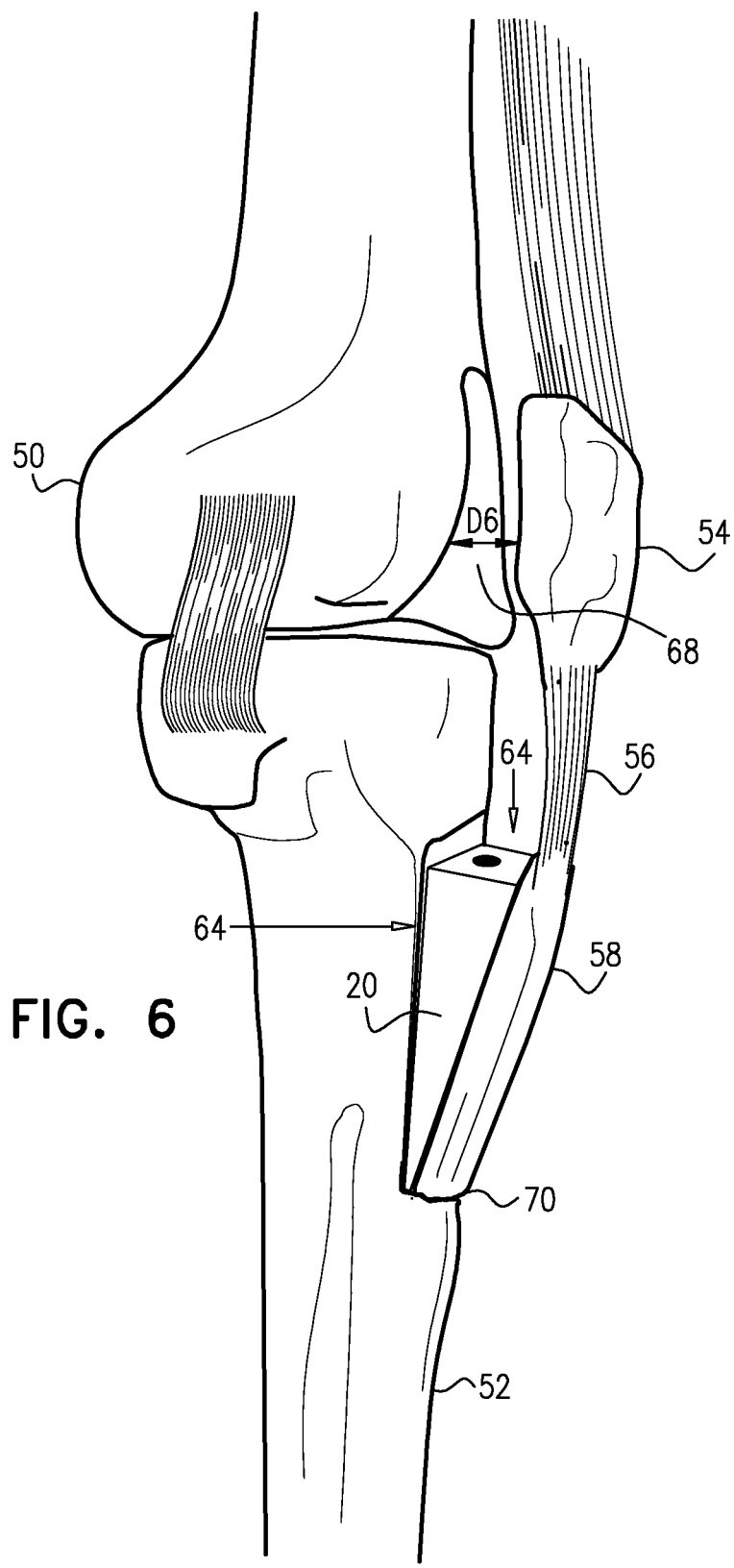
FIGS. 6-7 are schematic illustrations of an implant implanted in an osteotomy in a tibia of a subject, in accordance with some applications of the present invention.
Figure 7:
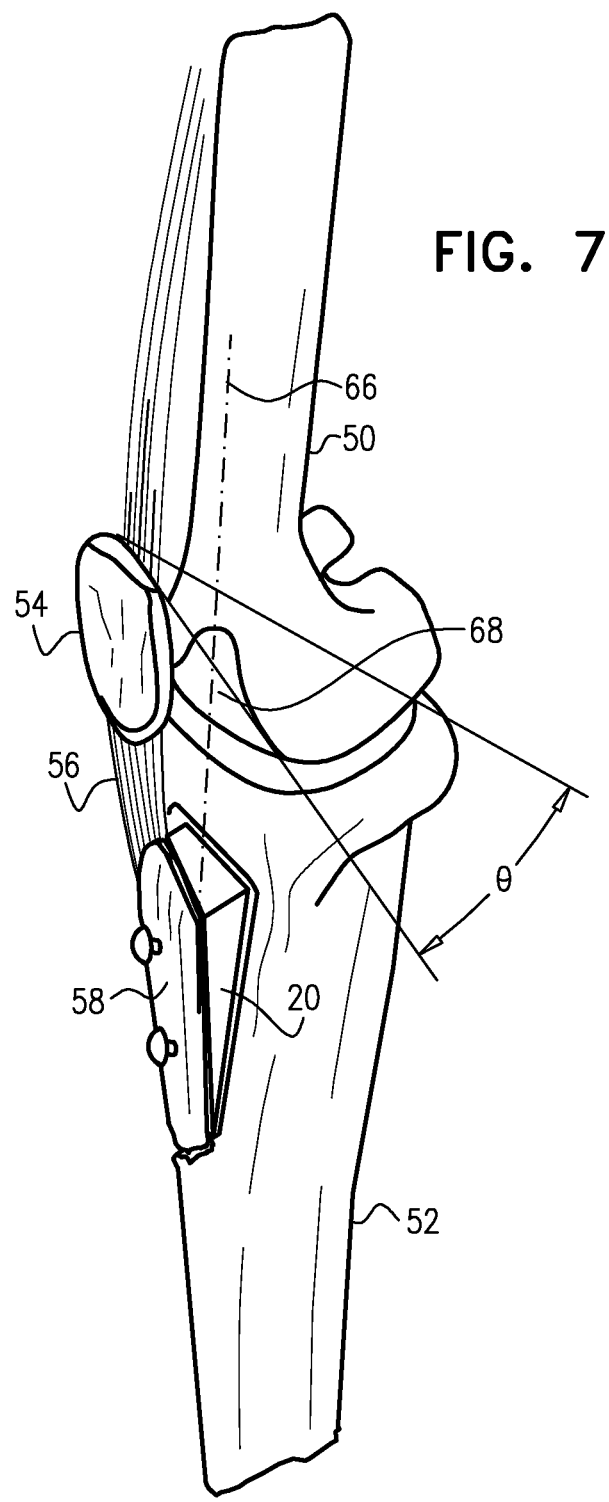

Reference is now made to FIGS. 6-7, which are schematic illustrations of implant 20 implanted in an osteotomy 64 in a tibia 52 of a subject, in accordance with some applications of the present invention.

Typically, prior to insertion of the implant, osteotomy 64 (FIG. 6) is created in the tibia. As shown in FIG. 7, the implant is then provided, and is inserted, along an axis of insertion 66, into the osteotomy. By inserting the implant in the osteotomy, tibial tuberosity 58 is rotated about axis of insertion 66, which results in a change in the angular orientation of the tibial tuberosity with respect to the other portion of the tibia. (As noted above, this rotation is facilitated by the distance between the top and bottom of the implant being greater at one side than at the other side.) Patellar tendon 56 transfers this rotational effect to patella 54, such that the patella is also rotated about axis of insertion 66, by an angle theta. Thus, the angular orientation of patella 54 is changed with respect to femur 50, and in particular, with respect to the trochlea 68 of the femur. As shown in FIG. 6, the insertion of the implant typically also increases a distance D6 of the patella from the trochlea, by pivoting the tibial tuberosity with respect to a point of contact 70 between the tibial tuberosity and the other portion of the tibia. (The pivoting of the tibial tuberosity increases a distance of the proximal portion of the tibial tuberosity from the other portion of the tibia, thus, via the patellar tendon, causing an increase in distance D6.)

As noted above, bone graft material, which is typically coupled to the implant, is typically inserted into the osteotomy, in order to help maintain the tibial tuberosity in its new position.

Reference is now made to FIGS. 8-10B, which are schematic illustrations of methods for operating on a subject, in accordance with some applications of the present invention. In some applications, by providing implant 20 and inserting it into an anatomical site, an angular orientation of a first portion of bone with respect to a second portion of bone is changed in two perpendicular planes in other words, by inserting the implant, the first portion of bone is made to rotate about (a) axis of insertion 66, and (b) an axis 86 that is perpendicular to the axis of insertion. The anatomical site is typically surrounded at least in part by one more bones. Typically, bone graft, material, e.g., bone graft, material that is coupled to the implant, is inserted into the anatomical site.

Figure 8:
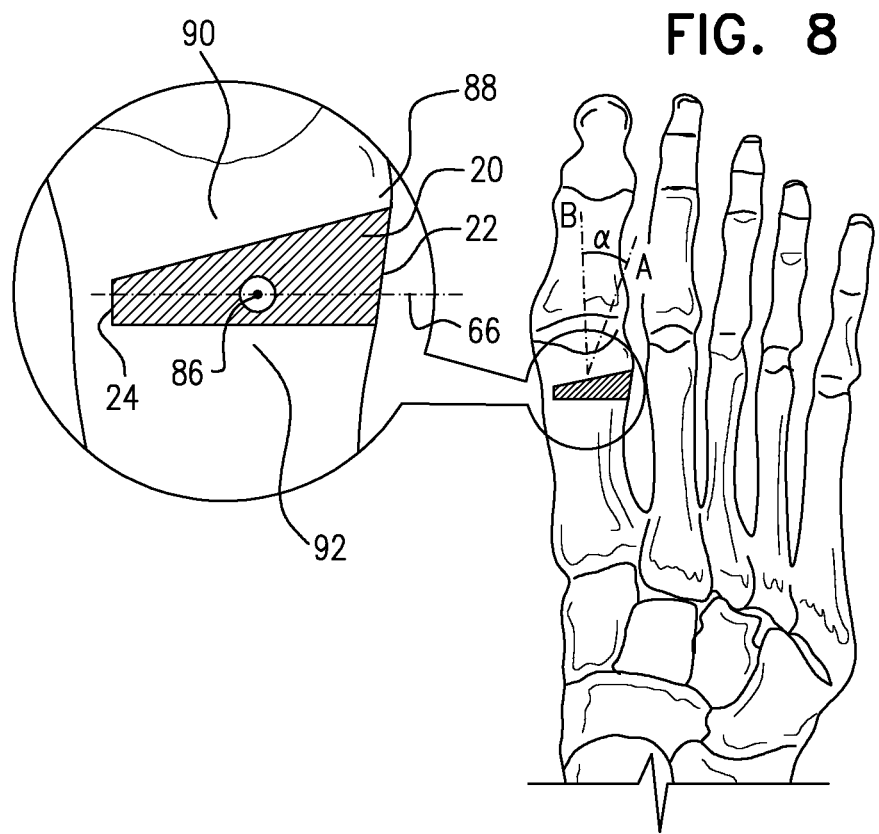
FIGS. 8, 9A-B, and 10A-B are schematic illustrations of methods for operating on a subject, in accordance with some applications of the present invention.

In FIG. 8, the anatomical site is a space within a metatarsal bone 88 of the subject. Typically, an osteotomy is created in metatarsal bone 88 prior to inserting the implant, and the implant is implanted in the osteotomy. FIG. 8 shows an application in which the implant is inserted from a lateral direction, such that axis of insertion 66 runs laterally along the page, and axis 86 runs into the page. The greater height at front end 22, relative to rear end 24, facilitates a rotation, by an angle alpha, of a first portion 90 of the metatarsal bone about axis 86. Furthermore, the greater height at one of the sides, relative to the other one of the sides, facilitates a rotation by an angle theta of first portion 90 about axis 66. (This latter rotation is not shown in FIG. 8; however, it is analogous to what is shown in FIG. 7.) Thus, the angular orientation of first portion 90 is changed, in two perpendicular planes, with respect to a second portion 92 of bone 88. (Furthermore, a distance of first portion 90 from second portion 92 is increased.) The method depicted in FIG. 8 may be used, for example, to treat metatarsus adductus.

Figure 9A:
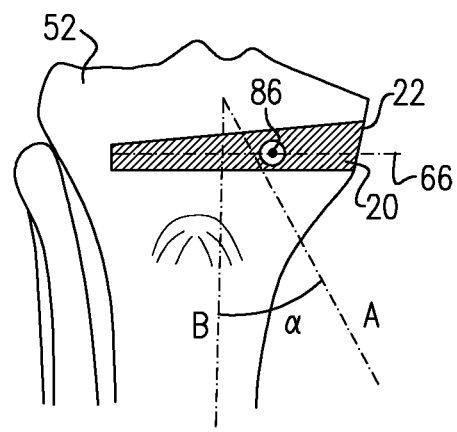
Figure 9B:
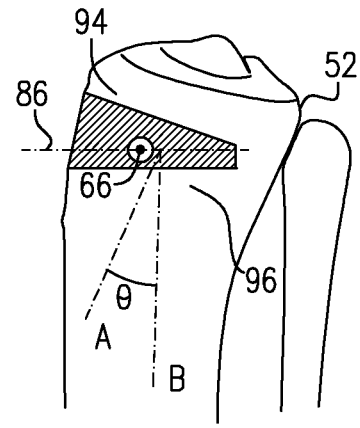

In FIGS. 9A-B, the anatomical site is a space within a tibia 52. FIG. 9A shows a frontal view of the tibia, while FIG. 9B shows a lateral view. Typically, an osteotomy is created in the tibia prior to inserting the implant. FIGS. 9A-B show an application in which the implant is inserted from a lateral direction, such that axis of insertion 66 runs laterally along the page in FIG. 9A, and into the page in FIG. 9B. The front-rear and side-side differences in height facilitate changing the angular orientation of a first portion 94 of the tibia with respect to a second portion 96 of the tibia that is more distal than first portion 94, by rotating first portion 94 about axes 66 and 86. The method depicted in FIGS. 9A-B may be used, for example, to treat varus or valgus knee.

Although FIGS. 8 and 9A-B depict a lateral insertion of the implant, it is noted that the scope of the present invention includes an insertion of the implant from other directions. (In such applications, axes 66 and 86 may be interchanged.)

Figure 10A:
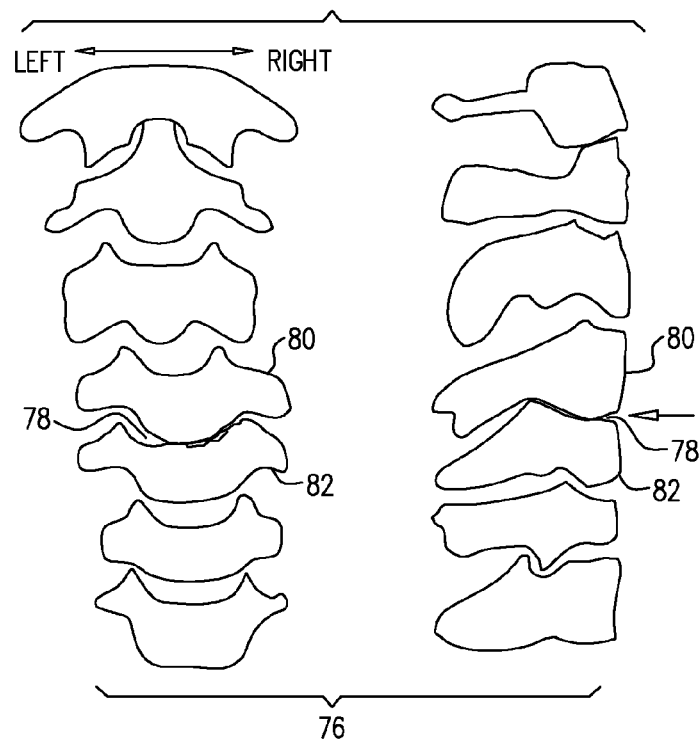
Figure 10B:
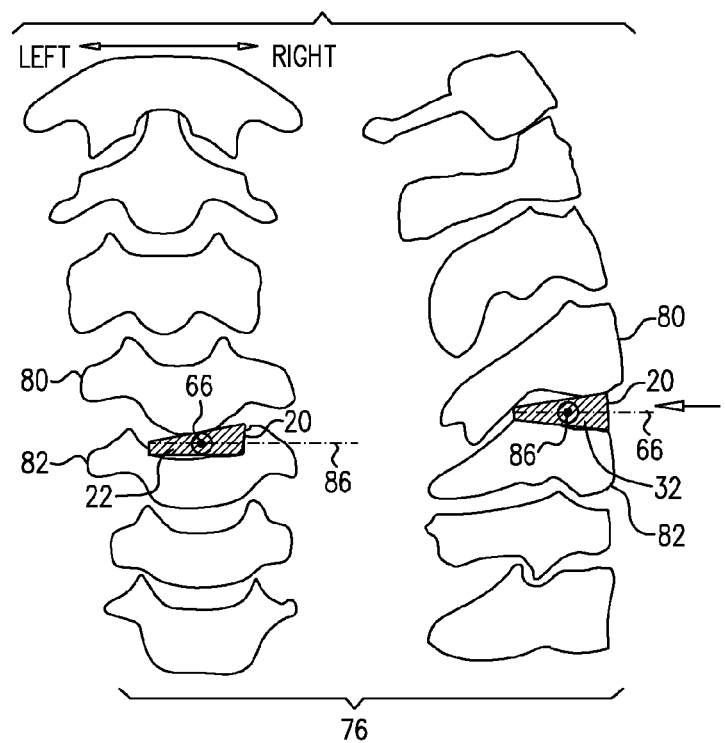

In FIGS. 10A-B, the anatomical site is a space between a first vertebra 80 and a second vertebra 82, in a cervical spine 76 of a subject. (The depicted method may also be performed on other portions of the spine.) FIG. 10A shows a frontal view (left) and lateral view (right) of spine 76 before implanting implant 20. Two pathological conditions may be observed: (i) an intervertebral space 78 between a first vertebra 80 and a second vertebra 82 of the subject is abnormally narrow, and is narrower at the right side of the spine than at the left side, and (ii) the spine is abnormally straight, i.e., normal lordosis (curvature of the spine) is lacking.

FIG. 10B shows the same two views of the spine following the implantation of the implant in intervertebral space 78. FIG. 10B shows an application in which the implant is inserted from the front or back of the spine, such that axis of insertion 66 runs into the page on the left, and laterally along the page on the right. The differences in height between the front and the rear of the implant, and between the two sides of the implant, facilitate changing the angular orientation of first vertebra 80 with respect to second vertebra 82, in addition to increasing the distance between the vertebrae. In particular, (i) due to the greater height of the implant at the right side of the implant, relative to the left side, the distance between the vertebrae is increased more at the right side than at the left side, thus restoring normal symmetry to the spinal column, and (ii) the greater height of the implant at the front of the implant, relative to the rear of the implant, facilitates the restoration of normal lordosis of the spine.

In some spinal applications, the subject lies on his back during the implantation in such applications, the implant may be "wedged," in an anterior-to-posterior direction, into the intervertebral space in other spinal applications, the subject lies on his front; in such applications, it is typically difficult to wedge the implant into the intervertebral space. Hence, in such applications, the intervertebral space is typically enlarged (by pulling the vertebra away from one another) before inserting the implant, in order to facilitate the insertion. Similarly, for applications in which the implant is not wedge-shaped (e.g., the height of the implant is constant), the intervertebral space may be enlarged prior to insertion of the implant.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for rotating a patella and increasing a distance of the patella from an associated trochlea of a femur of a subject, the method comprising:
   creating an osteotomy in a tibia of the subject;

inserting, along an axis of insertion, an orthopedic implant into the osteotomy, bone graft material being coupled to the orthopedic implant; and positioning the inserted orthopedic implant to:

cause rotation of the patella of the subject, via a patellar tendon of the subject, about the axis of insertion, by rotating a tuberosity of the tibia of the subject about the axis of insertion, and cause an increase in a distance of the patella from the trochlea of the femur of the subject, via the patellar tendon of the subject, by pivoting the tuberosity of the tibia with respect to a point of contact between the tuberosity of the tibia and another portion of the tibia, the orthopedic implant being shaped to define one or more passageways passing through the orthopedic implant.

2. The method according to claim 1, wherein the step of inserting the orthopedic implant into the osteotomy comprises changing an angular orientation of a first portion of bone with respect to a second portion of bone by rotating the first portion of bone about (a) the axis of insertion, and (b) an axis that is perpendicular to the axis of insertion.

3. The method according to claim 2, wherein the step of inserting the orthopedic implant into the osteotomy comprises increasing a distance of the first portion of bone from the second portion of bone.

4. The method according to claim 1, wherein the orthopedic implant includes a front end, a rear end, a top, a bottom, a right side, and a left side, the orthopedic implant being configured such that a distance between the top and the bottom is (a) greater at a first location at one of the right and left sides than at a second location opposite the first location at the other one of the right and left sides, and (b) greater at a third location at the front end than at a fourth location opposite the third location at the rear end.

5. A method for rotating a patella and increasing a distance of the patella from an associated trochlea of a femur of a subject, the method comprising:

creating an osteotomy in a tibia of the subject;

coupling bone graft material to an orthopedic implant;

inserting, along an axis of insertion, the orthopedic implant into the osteotomy:

positioning the inserted orthopedic implant to:

cause rotation of the patella, third bone member, via a patellar tendon of the subject, about the axis of insertion and a change in an angular orientation of a tuberosity of the tibia, first bone member, with respect to another portion of the tibia, second bone member, by rotating the tuberosity of the tibia about the axis of insertion, and increase a distance of the patella from the trochlea by pivoting the tuberosity of the tibia with respect to a point of contact between the tuberosity of the tibia and another portion of the tibia.

6. The method according to claim 5, wherein the step of coupling bone graft material to the orthopedic implant comprises coupling the bone graft material to the orthopedic implant prior to insertion of the orthopedic implant into the osteotomy.

7. The method according to claim 5, wherein the orthopedic implant is shaped to define one or more passageways passing through the orthopedic implant in which the bone graft material is disposed.

8. The method according to claim 5, wherein the orthopedic implant includes a front end, a rear end, a top, a bottom, a right side, and a left side, the orthopedic implant being configured such that a distance between the top and the bottom is (a) greater at a first location at one of the right and left sides than at a second location opposite the first location at the other one of the right and left sides, and (b) greater at a third location at the front end than at a fourth location opposite the third location at the rear end.

\* \* \* \* \*